United States Patent [19]

Kvita et al.

[11] 4,348,530

[45] Sep. 7, 1982

[54] THIOXANTHONECARBOXYLIC ACIDS, ESTERS, THIOESTERS AND AMIDES WITH REACTIVE FUNCTIONAL GROUPS

[75] Inventors: Vratislav Kvita, Reinach; Hans Zweifel, Basel; Martin Roth, Marly; Louis Felder, Basel, all of Switzerland

[73] Assignee: Ciba-Geigy Corporation, Ardsley, N.Y.

[21] Appl. No.: 228,533

[22] Filed: Jan. 26, 1981

[30] Foreign Application Priority Data

Feb. 5, 1980 [CH] Switzerland .................... 917/80

[51] Int. Cl.³ ............................................. C07D 335/16
[52] U.S. Cl. .................................. 549/27; 260/326.35
[58] Field of Search ....................... 549/27; 260/326.35

[56] References Cited

U.S. PATENT DOCUMENTS 3,856,789 12/1974 Fleming et al. ...................... 544/79
3,904,647 9/1975 Pfister et al. .......................... 549/27

FOREIGN PATENT DOCUMENTS 2811755 9/1978 Fed. Rep. of Germany .
46-31731 9/1971 Japan .
49-32796 9/1974 Japan .
1458185 12/1976 United Kingdom .

*Primary Examiner*—Richard Raymond
*Attorney, Agent, or Firm*—Michael W. Glynn

[57] ABSTRACT

Thioxanthone carboxylic acid esters, thioesters and amides with reactive functional groups of the formula

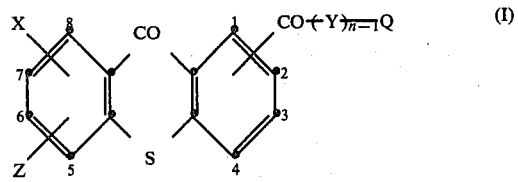

in which X, Y, Z, n and Q are as defined in the patent claim and Q is, for example, $-OCH=CH_2$, $-OCH_2CH=CH_2$, $-SCH_2CH=CH_2$ or $-NHCH_2CH=CH_2$ (n=1), $-OH$, $-SH$, $-NH_2$, $-COOH$, $-COCl$ or $-OCO-C(R'')=CH_2$, in which $R''$ is methyl or hydrogen (n=2), are suitable for the preparation of polymers with thioxanthone radicals in side chains. The compounds (I) and also the polymers which can be prepared therefrom can be employed as sensitisers for photocrosslinkable polymers or as initiators, if desired in a mixture with amines, for the photopolymerisation of ethylenically unsaturated compounds or for the photochemical crosslinking of polyolefines.

6 Claims, No Drawings

THIOXANTHONECARBOXYLIC ACIDS, ESTERS, THIOESTERS AND AMIDES WITH REACTIVE FUNCTIONAL GROUPS

The invention relates to novel thioxanthonecarboxylic acid esters, thioesters and amides with reactive functional groups, processes for their preparation and their use for the preparation of novel polymers with thioxanthone radicals in side chains. The thioxanthone derivatives according to the invention, and also the polymers prepared therefrom, can be used as sensitisers for photocrosslinkable polymers or as initiators, if desired in a mixture with amines, for the photopolymerisation of ethylenically unsaturated compounds or for photochemical crosslinking of polyolefines. It is known that unsubstituted or halogenated, especially chlorinated, thioxanthones are suitable as sensitisers for photoinduced crosslinking reactions. The prerequisite for a successful application of this type is good compatibility of the sensitiser in the polymer, i.e. miscibility of the sensitiser with the polymer must be such that elevated concentrations can be obtained. Furthermore, the sensitisers must be readily soluble in the solvents used when processing the polymers. The abovementioned known thioxanthones do not meet these requirements in every respect; in particular they easily separate out from the mixture in the polymer, as a result of which the sensitiser effect of the polymer is severely impaired.

Novel thioxanthone derivatives with reactive functional groups have now been found which are outstandingly suitable for use as sensitisers for photocrosslinkable polymers and in particular for the preparation of polymers which have thioxanthone radicals in side chains and which, in turn, are used as sensitisers for photocrosslinkable systems. The (monomeric) thioxanthone derivatives according to the invention are distinguished by good compatibility with the polymer and good solubility in conventional organic solvents. The polymers which can be prepared therefrom have, in particular, the advantage of a substantially lower tendency to separate out from mixtures with the photocrosslinkable systems to be sensitised (lower tendency to migration). Moreover, using the novel thioxanthone derivatives according to the invention, and the polymers which can be prepared therefrom, it is possible, surprisingly, so to influence UV absorption that these substances exert a sensitising effect even on irradiation with long-wave UV light (up to 450 nm) and thus effect crosslinking of the photosensitive polymers.

It is also known that the photopolymerisation of ethylenically unsaturated compounds can be initiated by aromatic ketones of the benzophenone, anthraquinone, xanthone and thioxanthone type. It has also been disclosed in U.S. Pat. No. 3,759,807 that the initiator effect of such aromatic ketones can be accelerated by the addition of organic amines. Since these amines on their own usually possess no initiator effect, they act in combination with aromatic ketones as activators or accelerators. Industrially, this is of great importance since the production rate of photochemically cured coatings or printing inks is primarily dependent on the rate of polymerisation of the unsaturated compound.

Mixtures of thioxanthone derivatives according to the invention, or the polymers which can be prepared therefrom, with organic amines as initiators for the photopolymerisation of ethylenically unsaturated compounds or for the photochemical crosslinking of polyolefines are distinguished by a high rate of polymerisation, a low tendency to yellowing in the case of coatings containing white pigments, and in some cases by good solubility in the substrate and/or high storage stability.

The thioxanthonecarboxylic acid esters, thioesters and amides according to the invention, which have reactive functional groups, have the formula I

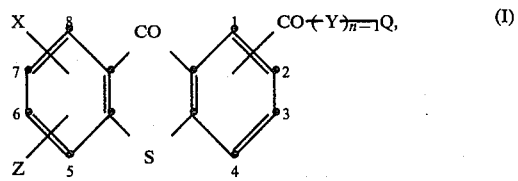

in which n is the number 1 or 2, X is hydrogen, halogen, —CN, —OH, —SH, —NO$_2$, —NH$_2$, phenylsulfonyl or alkylsulfonyl, alkyl, alkoxy, alkylthio, N,N-dialkylamino or —CO-alkyl having, in each case, 1-4 C atoms in the alkyl moieties, Z is hydrogen, halogen, —OH, —SH or alkyl, alkoxy, alkylthio or N,N-dialkylamino having, in each case, 1-4 C atoms in the alkyl moieties, Y is —OR$_1$—, —SR$_1$— or —N(R$_2$)R$_1$—, R$_1$ is straight-chain or branched alkylene having a total of 2-23 C atoms and 2-13 C atoms in the main chain, cyclopentylene, cyclohexylene, phenylene,

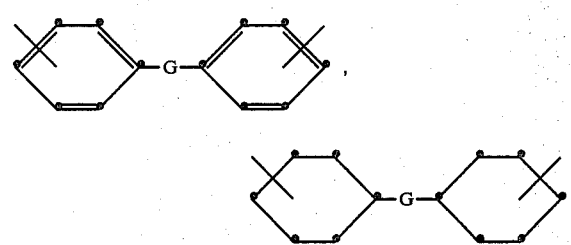

or, if n is 2 and Q is —OH or —OCO—C(R″)=CH$_2$, also —(CH$_2$CH$_2$O)$_x$—CH$_2$CH$_2$—, R$_2$ is hydrogen or straight-chain or branched alkyl having a total of 1-23 C atoms and 1-13 C atoms in the main chain, G is —CH$_2$—, —CH$_2$CH$_2$—, —C(CH$_3$)$_2$—, —O—, —SO$_2$— or —NH—, x is an integer from 1 to 5, Q is

—OCH$_2$—COOH, —OCH=CH$_2$, —OCH$_2$CH=CH$_2$, —SCH$_2$CH=CH$_2$ or —NHCH$_2$CH=CH$_2$ if n is 1, and is —OH, —SH, —NH$_2$, —NHR′, —SO$_3$H, —COOH, —COCl, —NCO, —OCO—C(R″)=CH$_2$, —SCO—C(R″)=CH$_2$, —NH-CO—C(R″)=CH$_2$, —OCH=CH$_2$,

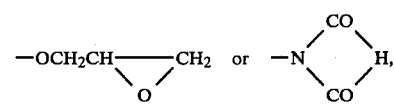

if n is 2, or is also —CH=CH$_2$ if R$_1$ is alkylene or phenylene, and R′ is alkyl having 1-5 C atoms and R″ is hydrogen or methyl. Compounds of the formula I in which Q is —NH$_2$ or —NHR′ can also be in the form of salts, especially salts with inorganic acids, such as H$_2$SO$_4$ or nitric acid and in particular HCl.

Alkyl, alkoxy or alkylthio groups X, Z, R' and $R_2$ and alkyl moieties in radicals X and Z can be straight-chain or branched. Alkylene groups $R_1$ and alkyl groups $R_2$ preferably have a total of not more than 18 and in particular not more than 12 C atoms.

Examples of alkyl, alkoxy, alkylthio, alkylsulfonyl, N,N-dialkylamino and —CO-alkyl groups X, Z, R' or $R_2$ according to the definition are: the methyl, ethyl, n-propyl, isopropyl, n-butyl, sec.-butyl, n-pentyl, 2- or 3-pentyl, n-hexyl, n-heptyl, 2- or 3-heptyl, n-octyl, n-nonyl, n-decyl, 2-decyl, n-dodecyl, n-tridecyl, tridec-7-yl, heptadec-9-yl, 2,6,10-trimethyldodecyl and 2,6,10,14-tetramethylhexadecyl groups; the methoxy, ethoxy, n-propoxy, isopropoxy and n-butoxy groups; the methylthio, ethylthio and n-propylthio groups; the methylsulfonyl and ethylsulfonyl groups; the N,N-dimethylamino, N,N-diethylamino, N-methyl-N-ethylamino and N,N-di-n-propylamino groups; and the acetyl, propionyl and butyryl groups.

Alkyl groups R', X and Z are preferably straight-chain and in particular have 1 or 2 C atoms.

Examples of alkylene groups $R_1$ according to the definition are: the 1,2-ethylene, propylene, tetramethylene, isobutylene, pentamethylene, iso- and neo-pentylene, hexamethylene, heptamethylene, 2- or 3-methylhexylene, octamethylene, nonamethylene, decamethylene, 2-methyl-nonylene, dodecamethylene, tridecamethylene, hexylheptylene, octylnonylene, 2,6,10-trimethyldecylene and 2,6,10,14-tetramethyl-dodecylene groups.

A cyclopentylene, cyclohexylene or phenylene group $R_1$ is, for example, the 1,3-cyclopentylene group, the 1,3- or in particular 1,4-cyclohexylene group or the 1,3- or 1,4-phenylene group. Preferred bicyclic radicals $R_1$ are those of the formulae

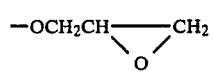

in which G is —CH$_2$—, —O— or —SO$_2$—.

$R_1$ is preferably alkylene having a total of 2-18 and in particular 2-12 C atoms, 1,3-cyclopentylene, 1,4-cyclohexylene, —CH$_2$CH$_2$OCH$_2$CH$_2$— or —(CH$_2$CH$_2$O)$_2$—CH$_2$CH$_2$—. $R_2$ is preferably hydrogen.

If n is 1, Q is preferably

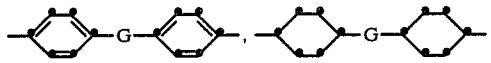

or or —OCH=CH$_2$, and if n is 2, Q is preferably —OH, —NH$_2$, —NHCH$_3$, —COOH, —COCl, —O-CO—C(R")=CH$_2$, —OCH=CH$_2$,

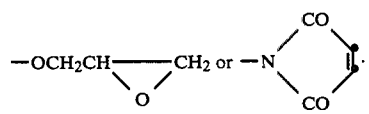

Preferred compounds of the formula I are, on the one hand, those in which Z is hydrogen and X, Y, Q and n are as defined under formula I. The grouping —CO—(Y)$_{\overline{n-1}}$Q is preferably bonded in the 1- or 3-position.

A further category of preferred compounds of the formula I comprises those in which X is bonded in the 6-position and is —NO$_2$, alkylsulfonyl having 1-4 and in particular 1 or 2 C atoms or phenylsulfonyl, Z is bonded in the 7-position and is alkyl, alkoxy, alkylthio or N,N-dialkylamino having, in each case, 1-4 and in particular 1 or 2 C atoms in the alkyl moieties, and the grouping —CO—(Y)$_{\overline{n-1}}$Q is in the 1-position or 3-position.

According to a further preference, Z is hydrogen and X is bonded in the 6-position and is —NO$_2$, alkylsulfonyl having 1-4 and in particular 1 or 2 C atoms or phenylsulfonyl. In this case the grouping —CO—(Y)$_{\overline{n-1}}$Q is likewise preferably bonded in the 1- and 3-position.

Very particularly preferred compounds of the formula I are those in which X is hydrogen and Z is hydrogen or methyl or methoxy bonded in the 7-position, and the group —CO—(Y)$_{\overline{n-1}}$Q is in the 1- or 3-position, and in particular those in which n is 1 and Q is

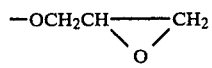

or —OCH=CH$_2$, or in which n is 2, Y is —OR$_1$— or —NHR$_1$—, R$_1$ is alkylene having 2-6 C atoms or, if Q is —OH or —OCO—C(R")=CH$_2$ also —CH$_2$C-H$_2$OCH$_2$CH$_2$— or —(CH$_2$CH$_2$O)$_2$CH$_2$CH$_2$—, and Q is —OH, —NH$_2$, —NHCH$_3$, —COOH, —COCl, —O-CO—C(R")=CH$_2$, —OCH=CH$_2$,

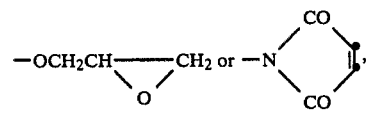

and also salts of those preferred compounds of the formula I in which Q is —NH$_2$ or —NHCH$_3$ with inorganic acids. Particularly preferentially, Q is —OCH=CH$_2$ if n is 1, and is —OH, —NH$_2$, —OCH=CH$_2$ or —OCO—C(R")=CH$_2$ if n is 2 and, if Q is —NH$_2$, salts with HCl are preferred.

The compounds of the formula I and their salts according to the definition can be prepared by (a) reacting a compound of the formula II

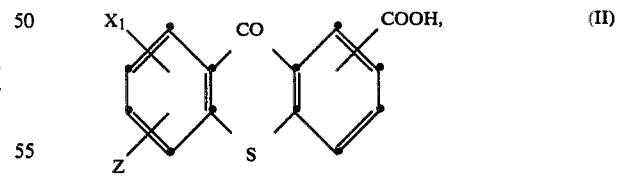

a C$_{1-6}$-alkyl ester of a compound of the formula II or an acid chloride of a compound of the formula II, in which Z and X$_1$ are not —SH or —OH, with a compound of the formula IIIa

or, if Q' is —NH$_2$ or —NHR', with a salt of a compound of the formula IIIa, to give a compound of the formula Ia

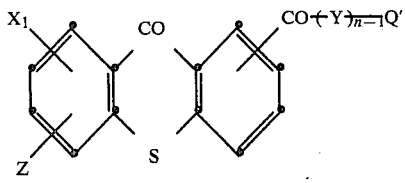 (Ia)

or corresponding salts, (b) reacting a compound of the formula II or a $C_{1-6}$-alkyl ester of a compound of the formula II with a compound of the formula IIIb $$CH_2=CH-OCO-R' \quad \text{(IIIb)}$$

to give a compound of the formula Ib

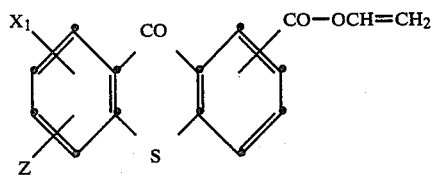 (Ib)

or (c) first reacting an acid chloride or a compound of the formula II with a salt of a compound of the formula III $$H\text{-}Y\text{-}NH_2 \quad \text{(IIIc)}$$

to give the corresponding salt of a compound of the formula IV

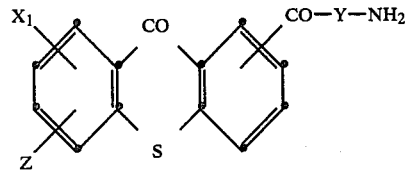 (IV)

and reacting the salt of a compound of the formula IV, in the presence of an inert organic solvent, with phosgene to give a compound of the formula Ic

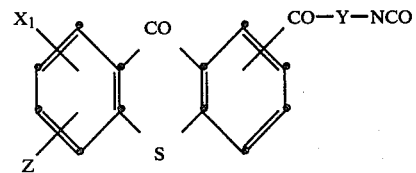 (Ic)

in which formulae Y, Z, R' and n are as defined under formula I, $X_1$ is hydrogen, halogen, —CN, —OH, —SH, —NO$_2$, phenylsulfonyl or alkylsulfonyl, alkyl, alkoxy, alkylthio, N,N-dialkylamino or —CO-alkyl having, in each case 1–4 C atoms in the alkyl moieties, Q' is

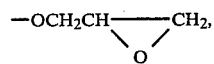

—OCH$_2$—COOH, —OCH$_2$CH=CH$_2$, —SCH$_2$CH=CH$_2$ or —NHCH$_2$CH=CH$_2$ if n is 1, and is —OH, —SH, —NH$_2$, —NHR', —SO$_3$H, —COOH, —OCO—C(R")=CH$_2$, —SCO—C(R")=CH$_2$, —NHCO—C(R")=CH$_2$,

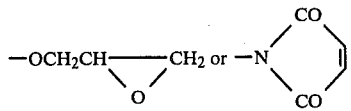

if n is 2, or is also —CH=CH$_2$ if R$_1$ is alkylene or phenylene, and R" is hydrogen or methyl, and, if desired, subsequently converting the group $X_1$ in the compounds of the formulae Ia, Ib or Ic into a group X which differs from $X_1$, and/or converting the group Q'=—COOH in formula Ia into the group —COCl by treatment with suitable chlorinating agents. Salts of compounds of the formulae IIIa, IIIc, Ia (Q'=—NH$_2$ or —NHR') and IV are, in particular, salts with inorganic acids such as H$_2$SO$_4$ or nitric acid and in particular HCl. Salts of compounds of the formula Ia in which Q' is —NH$_2$ or —NHR' can, if desired, be converted into the corresponding amines in a manner known per se, by the addition of suitable bases.

Only compounds of the formula II in which $X_1$ and Z are not —OH or —SH are suitable for conversion to the acid chlorides if desired. Examples of chlorinating agents which can be used are thionyl chloride, PCl$_5$ or oxalyl chloride. Alkyl esters, according to the definition, of compounds of the formula II are advantageously prepared from the corresponding acid chlorides.

The above reactions can be carried out in a manner known per se and, depending on the nature of the reactants, with or without the addition of inert organic solvents such as dioxan, benzene, toluene, methylene chloride or chloroform. Acid chlorides of compounds of the formula II are in general reacted with alcohols or thiols of the formula IIIa at temperatures between about 25° and 80° C. Advantageously, an excess of the corresponding alcohol or thiol is used as the solvent. The reaction of the acid chlorides of compounds of the formula II with amines of the formula IIIa is advantageously effected at temperatures between about 0° and 40° C. The reaction of the free acids of the formula II with alcohols of the formula IIIa is advantageously carried out with removal of the water by separation as an azeotrope and with the addition of catalytic amounts of an acid, such as H$_2$SO$_4$ or p-toluene-sulfonic acid, or in the presence of dehydrating agents, such as HCl gas or concentrated sulfuric acid. The entraining agent used is preferably benzene, toluene or chloroform. The transesterification of alkyl esters of compounds of the formula II is advantageously effected with the addition of acids, such as HCl or H$_2$SO$_4$, aluminium alcoholates or basic or acid ion exchangers. The reaction of compounds of the formula II, or their alkyl esters, with compounds of the formula IIIb is advantageously carried out in the presence of catalysts, such as HgCl$_2$, Li$_2$(PdCl$_4$) or PdCl$_2$.

Some compounds of the formula I can also be prepared by modified processes, for example as follows:

(1) Compounds of the formula I in which Y is —OR$_1$—, Q is

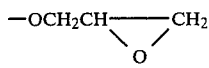

or —OCH₂CH=CH₂ if n is 1, and is —OH, —SH, —NH₂, —NHR', —OCO—C(R")=CH₂, —NH-CO—C(R")=CH₂, —SCO—C(R")=CH₂, —CH=CH₂, —OCH=CH₂ or

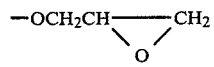

is n is 2, and X, Y and Z are as defined under formula I, by reacting an alkali metal salt or alkaline earth metal salt of a compound of the formula II, if necessary in the presence of a base, with a halide of the formula V

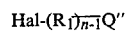        (V)

in which Hal is a halogen atom, especially chlorine or bromine, and Q" is

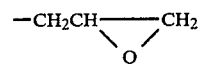

or —CH₂CH=CH₂ is n is 1, and —OH, —SH, —NH₂, —NHR', —OCO—C(R")=CH₂, —NH-CO—C(R")=CH₂, —SCO—C(R")=CH₂, —CH=CH₂, —OCH=CH₂ or

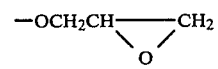

if n is 2, and $R_1$ and n are as defined above, and, if desired, subsequently converting the group $X_1$ into a group X which differs from $X_1$.

(2) Compounds of the formula I in which X, Y and Z are as defined but X and Z are not —OH, —SH or —NH₂, n is the number 2 and Q is

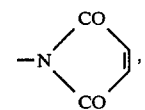

by reacting a compound of the formula IV, in which $X_1$ and Z are not —OH, —SH or —NH₂, with maleic anhydride, cyclising and resulting amidocarboxylic acid in a manner known per se, for example in the presence of acetic anhydride and sodium acetate, and, if desired, subsequently converting the group $X_1$ into a group X which differs from $X_1$.

(3) By reacting compounds of the formula I in which X, Y and Z are as defined but X and Z are not —OH, —SH or —NH₂, n is the number 2 and Q is —OH, —SH or —NH₂ with a halide of the formula VI

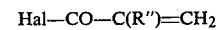        (VI)

in which Hal is a halogen atom, especially chlorine or bromine, and R" is as defined under formula I.

(4) Compounds of the formula I in which n is 2 or 1 and Q is

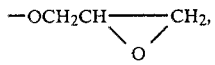

by reacting an alkali metal salt or alkaline earth metal salt of a compound of the formula Id

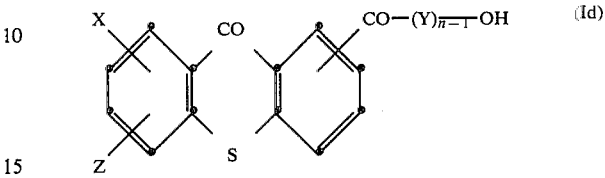       (Id)

in which n, X, Y and Z are as defined under formula I, with epichlorohydrin or epibromohydrin, if necessary in the presence of a base.

The alkali metal salts or alkaline earth metal salts of compounds of the formula II or Id which are used in the above reactions are, for example, calcium salts or barium salts and in particular sodium salts or potassium salts. Bases which can be used are, for example, amines, such as diethylamine and triethylamine.

Reactions (1) and (4) can also be carried out by means of phase transfer catalysis, for example in the presence of tetra-alkyl- or trialkylbenzyl-ammonium halides having, in each case, 1–4 C atoms in the alkyl moieties, and $K_2CO_3$ or $Na_2CO_3$.

The starting compounds of the formulae IIIa, IIIb and IIIc are known or can be prepared by methods known per se. Some of the compounds of the formula II are also known. They can be prepared in a manner known per se (cf. German Offenlegungsschrift No. 2,344,799 and U.S. Pat. No. 4,101,558), for example by cyclising a compound of the formula VIIa or VIIb

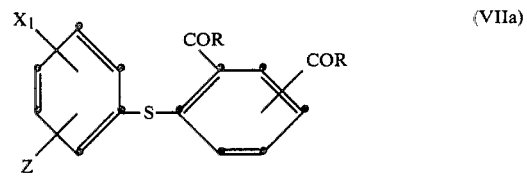       (VIIa)

or

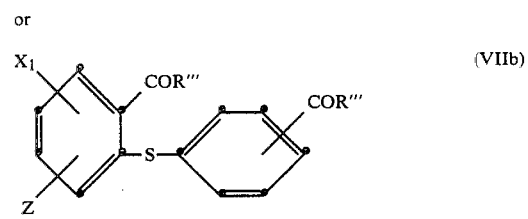       (VIIb)

in which $X_1$ and Z are as defined above and R and R''' are —OH or, if Z and $X_1$ are not —OH or —SH, also chlorine, or, if the —COR groups are in the ortho-position relative to one another, the two Rs together can be —O—, with simultaneous hydrolysis of chlorine atoms R or R'''.

Starting materials of the formula II in which $X_1$ is hydrogen, halogen, —CN, —NO₂, phenylsulfonyl, alkylsulfonyl, alkyl, alkoxy, alkylthio or N,N-dialkylamino having, in each case, 1–4 C atoms in the alkyl moieties and Z is hydrogen, halogen or alkyl, alkoxy, alkylthio or N,N-dialkylamino having, in each case, 1–4 C atoms in the alkyl moieties can also be prepared by (α) cyclising a compound of the formula VIIIa

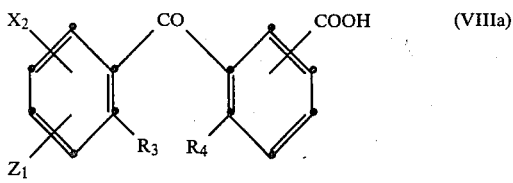

in which $Z_1$ is hydrogen, halogen or alkyl, alkoxy, alkylthio or N,N-dialkylamino having, in each case, 1–4 C atoms in the alkyl moieties, $X_2$ is hydrogen, halogen, —CN, —NO$_2$, phenylsulfonyl or alkylsulfonyl, alkyl, alkoxy, alkylthio or N,N-dialkylamino having, in each case, 1–4 C atoms in the alkyl moieties, one of $R_3$ and $R_4$ is a mercapto group and the other is a detachable group, or (β) cyclising a compound of the formula VIIIb

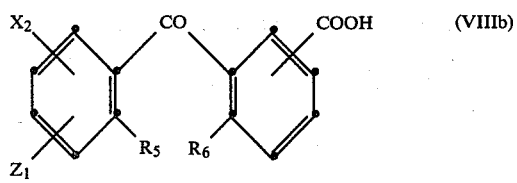

in which $X_2$ and $Z_1$ are as defined above and $R_5$ and $R_6$ independently of one another are a detachable group, with an inorganic sulfide to give a compound of the formula II.

Finally, starting compounds of the formula II in which $X_1$ is hydrogen, halogen, —NO$_2$, phenylsulfonyl or alkylsulfonyl, alkyl, alkoxy, alkylthio, N,N-dialkylamino or —CO-alkyl having, in each case, 1–4 C atoms in the alkyl moieties and Z is hydrogen, halogen or alkyl, alkoxy, alkylthio or N,N-dialkylamino having, in each case, 1–4 C atoms in the alkyl moieties can also be obtained by reacting a compound of the formula IX

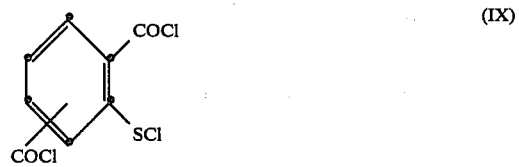

in the presence of a Friedel-Crafts catalyst, with a compound of the formula X

in which $X_3$ is hydrogen, halogen, —NO$_2$, phenylsulfonyl or alkylsulfonyl, alkyl, alkoxy, alkylthio, N,N-dialkylamino or —CO-alkyl having, in each case, 1–4 C atoms in the alkyl moieties and $Z_1$ is as defined above, and decomposing the resulting complex to give a compound of the formula II.

The cyclisation of the compounds of the formulae VIIa and VIIb is advantageously carried out in the presence of a proton acid or of a Lewis acid. Examples of suitable proton acids are polyphosphoric acid, if desired in a mixture with phosphorus oxychloride, chlorosulfonic acid and sulfuric acid. Suitable Lewis acids are, for example, aluminium trichloride or boron trifluoride.

The starting compounds of the formulae VIIa and VIIb can, for example, be prepared analogously to the procedures described in German Offenlegungsschrift No. 2,344,799, by reacting suitably substituted thiophenols or derivatives thereof, such as alkali metal salts or alkaline earth metal salts, with nitrobenzenes or halogenobenzenes. For this reaction, the thiophenol and the nitro- or halogenobenzene together must have at least two —COR''' or —COR''' groups, or two groups which can be converted to —COR or —COR''' groups, such as nitrile groups, and one of these groups must be in the ortho-position relative to the SH group or to the nitro group or to a halogen atom.

Suitable nitrobenzenes are those which, in addition to the nitro group, also contain one or more electron-attracting groups, such as carboxylic acid ester groups, carboxylic acid chloride groups, nitrile groups, anhydride groups or imide groups. According to a preferred process, compounds of the formula VIIa are prepared by reacting a dicarboxylic acid alkyl ester of nitrophthalic acid, nitroisophthalic acid or nitroterephthalic acid with a suitably substituted thiophenol and then saponifying the resulting dicarboxylic acid alkyl ester of a compound of the formula VIIa.

Detachable groups $R_3$ to $R_6$ are, in particular, halogen atoms and nitro, arylsulfonyl and sulfinyl groups. Preferred detachable groups $R_3$ to $R_6$ are halogen atoms, especially chlorine, and nitro groups.

The inorganic sulfide used for reaction with compounds of the formula VIIIb is advantageously an alkali metal sulfide or hydrosulfide or alkaline earth metal sulfide or hydrosulfide, preferably sodium sulfide. The starting materials of the formulae VIIIa and VIIIb can be obtained in a manner known per se, by Friedel-Crafts reaction of correspondingly substituted acyl halides with suitably substituted nucleophilic aromatic compounds.

The condensation reaction of the compounds of the formula IX with the compounds of the formula X in the presence of Friedel-Crafts catalysts, especially aluminium trichloride, is advantageously carried out in an organic medium at temperatures between about 10° and 80° C. After the reaction has ended, the resulting complex can be decomposed by pouring into a water/ice mixture or by adding dilute mineral acid, such as hydrochloric acid, or aqueous solutions of an alkali metal hydroxide or alkaline earth metal hydroxide, such as sodium hydroxide, potassium hydroxide, barium hydroxide or calcium hydroxide.

The conversion of groups $X_1$, $X_2$ or $X_3$ to groups X can be carried out in a manner known per se. Thus, for example, nitro groups $X_1$, $X_2$ or $X_3$ can be reduced, by methods known per se, to amino groups, which, in turn, can be converted to halogen atoms or —OH, —SH, —CN, alkoxy or N,N-dialkylamino groups. Cyano groups $X_1$ or $X_2$ can be converted to —CO-alkyl groups X. Thioxanthones of the formula I which are substituted by alkylsulfonyl or phenylsulfonyl groups can be prepared, for example, by reacting the corresponding nitro compounds with alkali metal alkyl sulfinates or alkali metal phenyl sulfinates.

By virtue of the reactive functional groups Q, the thioxanthone derivatives, according to the invention, of the formula I are particularly suitable for the preparation of polymers, which, in turn, are used as sensitisers for photocrosslinkable systems (polymers) or as photoinitiators. The invention thus also relates to polymers which have a mean molecular weight of not less than 1,000 and carry, in side chains, thioxanthone groupings of the formula I'

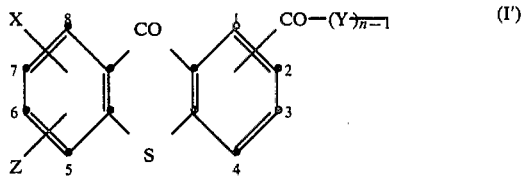

in which X, Y, Z and n are as defined under formula I, the proportion of groupings of the formula I' being not less than 2 percent, preferably 2–100 and in particular 20–100 percent, based on the number of recurring structural elements in the polymer.

The polymers according to the invention advantageously have a mean molecular weight of not less than 1,000 to 500,000, and in particular a mean molecular weight of about 1,000 to 100,000.

The mean molecular weight is determined by methods known per se, for example by determining the light scatter or by gel permeation chromatography.

The polymers according to the invention are, for example, polyethers, polyamines, polyimines, polycondensation products based on phenol-formaldehydes, polysaccharides, gelatines and, in particular, polymers which are obtained by homopolymerisation or copolymerisation of monomers containing C=C double bonds.

The polymers according to the invention can be prepared by synthesis methods known per se for the preparation of macromolecules with side groups. In principle, the following routes can be used:

1. Incorporation of the thioxanthone radicals of the formula I' into an existing polymer chain;
2. Build-up of the polymer chain from monomers which already contain the thioxanthone grouping of the formula I', in which case the polymer chain can be built up by polymerisation or polyaddition.

In some cases, identical products can be obtained by method 1 and method 2, so that, depending on the nature of the functional groups, it is possible to use method 1 or method 2 as desired. If the thioxanthone radicals are incorporated into an already existing polymer chain, this incorporation is effected either by a condensation reaction or by an addition reaction with simultaneous opening of a ring system, for example of a dicarboxylic acid anhydride group or of an epoxide group.

In accordance with the abovementioned build-up method, polymers according to the invention can be prepared by reacting a compound of the formula Ie

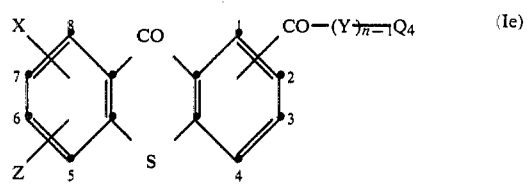

in which $Q_4$ is $-OCH=CH_2$, $-OCH_2CH=CH_2$, $-SCH_2CH=CH_2$ or $-NHCH_2CH=CH_2$ if n is 1, and is $-OCO-C(R'')=CH_2$, $-SCO-C(R'')=CH_2$, $-NHCO-C(R'')=CH_2$, $-OCH=CH_2$ or

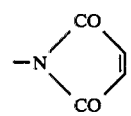

if n is 2, or is also $-CH=CH_2$ if $R_1$ is alkylene or phenylene, and X, Y, Z, R'' and n are as defined under formula I, if desired in the presence of comonomers, the molar ratio of the compound of the formula Ie to the comonomers being 1:49 to 1:0.

$Q_4$ is preferably

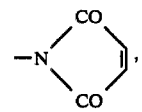

$-OCH=CH_2$ or $-OCO-C(R'')=CH_2$.

In accordance with the abovementioned incorporation method, polymers according to the invention can be prepared, for example, by reacting a compound of the formula If

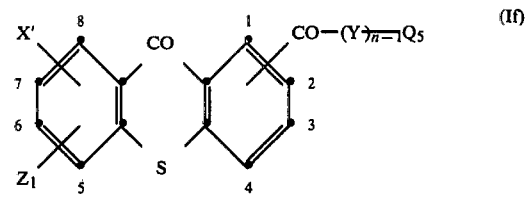

in which X' is hydrogen, halogen, $-CN$, $-NO_2$, phenylsulfonyl or alkylsulfonyl, alkyl, alkoxy, alkylthio, N,N-dialkylamino or $-CO$-alkyl having, in each case, 1–4 C atoms in the alkyl moieties, $Z_1$ is hydrogen, halogen or alkyl, alkoxy, alkylthio or N,N-dialkylamino having, in each case, 1–4 C atoms in the alkyl moieties, and $Q_5$ is

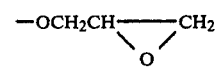

or $-OCH_2-COOH$ if n is 1, and is $-OH$, $-SH$, $-NH_2$, $-NHR'$, $-SO_3H$, $-COOH$, $-COCl$, $-NCO$ or

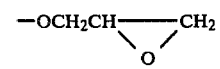

if n is 2, and Y, R' and n are as defined under formula I, or salts of compounds of the formula If, in which $Q_5$ is —$NH_2$ or —NHR', with a polymer containing corresponding functional groups, in a ratio of 1:50 to 1:1, based on the number of recurring structural elements in the polymer.

Compounds of the formula If in which $Q_5$ is —COOH, —COCl, —$SO_3H$ or —$OCH_2COOH$ can, for example, be reacted with polymers which contain free OH, $NH_2$, NH-alkyl or SH groups. Compounds of the formula If in which $Q_5$ is —OH, —SH, —$NH_2$, —NHR', —NCO or

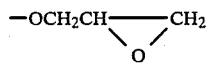

are suitable, for example, for reaction with polymers which contain anhydride or —COOH groups. Finally, compounds of the formula If in which $Q_5$ is —OH, —SH, —$NH_2$, —NHR' or —COOH can also be reacted with polymers which contain

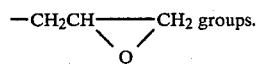 groups.

Compounds of the formula Ie are suitable for homopolymerisation or for copolymerisation with other ethylenically unsaturated comonomers, especially those of the type indicated further below.

Examples of starting polymers which can be reacted with compounds of the formula If are: polyacrylic acid, polymethacrylic acid, copolymers of these acids and other ethylenically unsaturated monomers, copolymers built up from maleic anhydride and ethylenically unsaturated monomers, such as methyl vinyl ether, ethylene, styrene, hex-1-ene, dec-1-ene, tetradec-1-ene and octadec-1-ene, polymers having free hydroxyl groups, such as homopolymers and copolymers of hydroxyalkyl acrylates and hydroxyalkyl methacrylates, polyvinyl alcohols, natural or regenerated cellulose, cellulose derivatives, hydroxyalkylcellulose, polyethers having free —OH groups, phenol-formaldehyde polycondensation products, polymers having free glycidyl groups, such as copolymers based on glycidyl acrylates and glycidyl methacrylates, polyethyleneimines and polymers with free amino groups in side chains, for example poly-p-aminostyrene.

Preferred polymers according to the invention are those which have a mean molecular weight of about 1,000 to 100,000 and contain recurring structural elements of the formula XI to XX

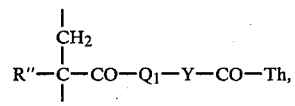 (XI)

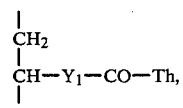 (XII)

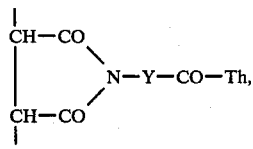 (XIII)

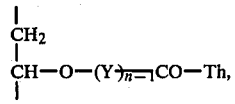 (XIV)

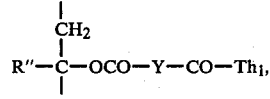 (XV)

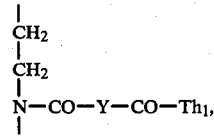 (XVI)

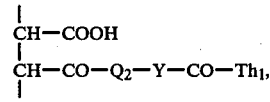 (XVII)

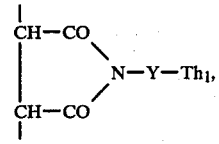 (XVIIa)

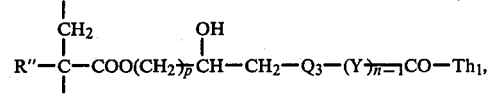 (XVIII)

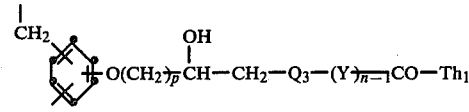 (XIX)

or

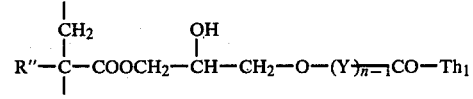 (XX)

in which "Th" is a radical of the formula I"

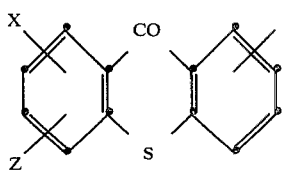

and "Th₁" is a radical of the formula I'''

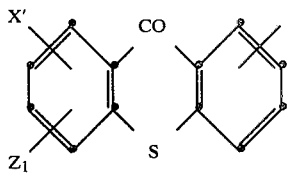

X, Y, Z, R" and n are as defined under formula I and X' and Z₁ are as defined under formula If, Q₁ is —O—, —S— or —NH—, Q₂ is —O—, —S—, —NH— or —NR'—, Q₃ is —OCO—, —O—, —S—, —NH— or —NR'—, R' is alkyl having 1-5 C atoms, p is the number 1 or 2, Y₁ is —OR₁—, —SR₁— or —NHR₁— and R₁ is straight-chain or branched alkylene having a total of 2-23 C atoms and 2-13 C atoms in the main chain, or phenylene.

If the polymers according to the invention are copolymers, these preferably consist of recurring structural elements of the formulae XI to XX and of identical or different recurring structural elements of the formula XXI

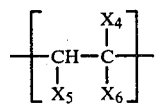

in which X₅ is hydrogen, X₄ is hydrogen, chlorine or methyl, X₆ is hydrogen, methyl, chlorine, CN, —COOH, —CONH₂, phenyl, methylphenyl, methoxyphenyl, cyclohexyl, pyridyl, imidazolyl, pyrrolidyl, —COO-alkyl having 1-12 C atoms in the alkyl moiety, —COO-phenyl,

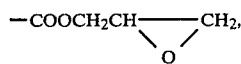

—COO-alkyl—OH having 1-3 C atoms in the alkyl moiety, —OCO-alkyl having 1-4 C atoms in the alkyl moiety, —OCO-phenyl, —CO-alkyl having 1-3 C atoms in the alkyl, alkoxy having 1-20 C atoms or phenoxy, or X₄ is hydrogen and X₅ and X₆ together are the grouping —CO—O—CO— or are each —COOH or —COO-alkyl having 1-6 C atoms in the alkyl. Preferably, X₅ is hydrogen; X₄ is hydrogen or methyl and X₆ is hydrogen, —OCOCH₃, —COOH or —COO-alkyl having 1-8 C atoms in the alkyl, or X₄ and X₅ are each hydrogen and X₆ is —CN, chlorine, phenyl or alkoxy having 1-6 C atoms, especially methoxy, or X₄ is hydrogen and X₅ and X₆ together form the grouping —CO—O—CO—.

In the above formulae I', I", Ie, If and XI to XX, X and X', Z and Z₁, n, Y and Q₄ and Q₅ have the corresponding preferred meanings defined above, and the groupings —CO—(Y)ₙ₋₁—, or —CO—(Y)ₙ₋₁Q₄ and —CO—(Y)ₙ₋₁Q₅ are preferably bonded to the benzene ring in the 1-position or 3-position. Particularly preferred polymers are those having recurring structural elements of the formulae XI, XIII to XV or XVII to XX and in particular polymers which have recurrinng structural elements of the formulae XI, XIV or XVII and, if desired, identical or different recurring structural elements of the formula XXI, in which formulae R" is hydrogen or methyl, Q₁ is —O—, Q₂ and Q₃ independently of one another are —O— or —NH—, p is the number 1, n is the number 1 or 2, Y is —OR₁— or —NHR₁—, R₁ is alkylene having 2-6 C atoms or, if Q₂ is —O—, also —CH₂CH₂OCH₂CH₂— or —(CH₂CH₂O)₂—CH₂CH₂—, X and X' are hydrogen, Z and Z₁ are hydrogen or methyl or methoxy bonded in the 7-position, X₅ is hydrogen, X₄ is hydrogen or methyl and X₆ is hydrogen, —OCOCH₃, —COOH or —COO-alkyl having 1-8 C atoms in the alkyl, or X₄ and X₅ are each hydrogen and X₆ is —CN, chlorine, phenyl or alkoxy having 1-6 C atoms, especially methoxy, or, if X₄ is hydrogen, X₅ and X₆ together are also —CO—O—CO—, and the groupings —CO—(Y)ₙ₋₁ are bonded in the 1-position or 3-position to the benzene ring of the radical "Th" or "Th₁". Of the radicals X₄ to X₆, X₄ and X₅ are particularly preferentially hydrogen and X₆ is particularly preferentially hydrogen, —COOH or C₁₋₆-alkoxy, especially methoxy, if desired in combination with structural elements of the formula XXI in which X₄ is hydrogen and X₅ and X₆ together are —CO—O—CO—.

Polymers with recurring structural elements of the formulae XI to XIV can be obtained by polymerising a compound of the formula Ie, in which X, Y, Z, Q₄ and n are as defined above, if desired in the presence of ethylenically unsaturated comonomers, especially those of the formula XXIa

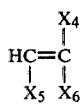

in which X₄, X₅ and X₆ are as defined under formula XXI, the molar ratio of compounds of the formula Ie to comonomers being 1:49 to 1:0 and in particular 1:4 to 1:0. Particularly preferentially, acrylic acid is used as the comonomer.

Polymers with recurring structural elements of the formulae XV to XX can be obtained by (i) reacting a compound of the formula If, in which X', Z₁ and Y are as defined, Q₅ is —COOH or —COCl and n is the number 2, with a polymer containing recurring structural elements of the formulae XVa or XVIa

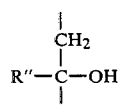

or

-continued

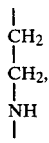
(XVIa)

(ii) reacting a compound of the formula If, in which X', $Z_1$ and Y are as defined, $Q_5$ is —OH, —SH, —NH$_2$, —NHR' or —NCO and n is the number 2, with a polymer containing recurring structural elements of the formula XVIIa

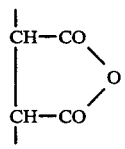
(XVIIa)

(iii) reacting a compound of the formula If, in which X', $Z_1$ and Y are as defined, and $Q_5$ is —OH, —SH, —NH$_2$, —NHR' or —COOH and n is the number 2, with a polymer containing recurring structural elements of the formula XVIIIa or XIXa

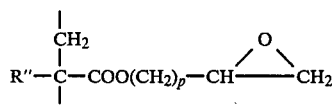
(XVIIIa)

or

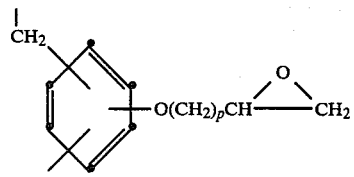
(XIXa)

in which p and R" are as defined under the formulae XVIII and XIX, or (iv) reacting a compound of the formula If, in which X', $Z_1$ and Y are as defined, n is the number 1 or 2 and $Q_5$ is

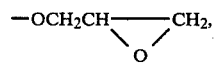

with a polymer containing recurring structural elements of the formula XXa

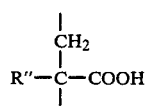
(XXa)

in which R" is as defined above, the ratio of the polymer:compound of the formula If being 1:50 to 1:1, especially 1:5 to 1:1, based on the number of recurring structural elements in the polymer. Particularly preferred polymers are polyacrylic acid and maleic anhydride/ethylene and maleic anhydride/methyl vinyl ether copolymers.

The incorporation of thioxanthone derivatives according to the invention into existing polymer chains by means of a condensation reaction or addition reaction can be effected in a manner known per se, advantageously at temperatures of about −50° C. to +150° C. and if desired in the presence of an acid-binding agent, if salts, according to the definition, of compounds of the formula I are employed. The reaction is preferably carried out in an inert organic solvent or a solvent mixture, and in the case of condensation reactions is preferably carried out at temperatures of about −20° C. to +100° C. Addition reactions are advantageously carried out at elevated temperature, in general at temperatures between about 80° and 120° C. or at the reflux temperature.

Suitable solvents for carrying out the condensation reactions and addition reactions are, for example: aliphatic or cyclic ketones, such as acetone, methyl ethyl ketone, isopropyl methyl ketone, cyclohexanone, cyclopentanone and γ-butyrolactone; cyclic ethers, such as tetrahydrofuran, tetrahydropyran or dioxan; cyclic amides, such as N-methyl-2-pyrrolidone, N-ethyl-2-pyrrolidone or N-methyl-ε-caprolactam; N,N-dialkylamides of aliphatic monocarboxylic acids having 1–3 C atoms in the acid moiety, such as N,N-dimethylformamide, N,N-dimethylacetamide, N,N-diethylacetamide or N,N-dimethylmethoxyacetamide; pyridine and pyridine bases or tertiary amines, in particular trialkylamines and dialkylbenzylamines having, preferably, 1–4 C atoms in the alkyl moieties, for example triethylamine and diethylbenzylamine; and dialkylsulfoxides, such as dimethylsulfoxide and diethylsulfoxide.

Preferred solvents for condensation reactions are cyclic amides and N,N-dialkylamides of the abovementioned type, especially N-methyl-2-pyrrolidone, N,N-dimethylformamide and N,N-dimethylacetamide. For addition reactions, cyclic ethers and cyclic ketones, in particular tetrahydrofuran and cyclohexanone, and also pyridine are preferred.

The homopolymerisation of compounds of the formula Ie, and also the copolymerisation of these compounds with other ethylenically unsaturated monomers, for example of the formula XXIa, can likewise be carried out in a manner known per se, for example in the presence of conventional cationic and anionic initiators. Free radical polymerisation is preferred. Advantageously, free radical initiators known per se, such as inorganic or organic peroxides or azo compounds, for example hydrogen peroxide, potassium peroxydisulfate, tert.-butyl hydroperoxide, di-tert.-butyl peroxide, peracetic acid, benzoyl peroxide, diacyl peroxide, cumene hydroperoxide, tert.-butyl perbenzoate, tert.-alkyl peroxycarbonates and α,α'-azoisobutyronitrile, are used in amounts of about 0.01 to 5% by weight and preferably 0.01 to 1.5% by weight, based on the total weight of monomers. The reaction temperatures for free radical polymerisation are in general between about 30° and 100° C. However, free radical polymerisation can also be carried out in the cold, and redox systems in the abovementioned concentrations can also be used for this purpose, for example mixtures of peroxides, such as hydrogen peroxide, and a reducing agent, such as divalent iron ions.

The polymerisation can be carried out in homogeneous phase, for example in bulk (block polymerisation) or in solution, or in heterogeneous phase, i.e. as precipitation polymerisation, emulsion polymerisation or suspension polymerisation. Polymerisation in solution is preferred.

Suitable solvents are those of the type mentioned for the condensation reaction or addition reaction and also: halogenated aliphatic hydrocarbons, such as methylene chloride, chloroform, tetrachloroethane and tetrachloroethylene; alkyl esters of aliphatic monocarboxylic acids having a total of 2-6 C atoms, such as methyl formate, ethyl formate and n-butyl formate or methyl acetate, ethyl acetate and n-butyl acetate; and ethylene glycol dialkyl ethers having 1-4 C atoms in the alkyl moieties, such as ethylene glycol dimethyl ether, ethylene glycol diethyl ether and ethylene glycol di-n-butyl ether.

The compounds, according to the invention, of the formula I can also be used as such as sensitisers for photocrosslinkable polymers of the most diverse types.

Such polymers are used, for example, for the production of printing plates for the offset printing process and for the preparation of photo-offset lacquers, for unconventional photography, for example for the production of photographic images by means of photopolymerisation or photocrosslinking. Such polymers are used, in particular, as so-called photoresists for the production of printed circuits by methods known per se. For this purpose, that side of the printed board assembly which is provided with the light-sensitive coating is exposed through a slide negative carrying the conductive pattern and then developed, after which the unexposed areas of the coating are removed using developer fluid.

The polymers which can be used are, in themselves, any desired materials for which the sensitivity to light (sensitivity to actinic radiation) can be increased by the of the sensitisers according to the invention. The compounds of the formula I and the polymers prepared therefrom are very particularly suitable as sensitisers for polymers of the type described in German Offenlegungsschrift No. 2,626,769, i.e. polymers which contain, as light-sensitive groups, groups of the formula XXII

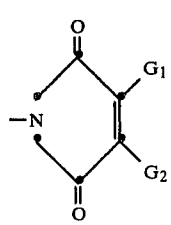

(XXII)

in which $G_1$ and $G_2$ independently of one another are alkyl having 1-4 C atoms, especially methyl, or $G_1$ and $G_2$ together are the members required to complete a five-membered to six-membered carbocyclic ring.

The compounds of the formula I and the polymers which can be prepared therefrom can be incorporated into the photocrosslinkable polymers in a manner known per se. The sensitiser content in the polymer can vary greatly, depending on the intended use and the number of photocrosslinkable groups present in the polymer, but in general is between about 0.1 and 20%, based on the weight of the polymer.

Finally, the thioxanthone derivatives, according to the invention, of the formula I, and also the polymers which can be prepared therefrom and have side groupings of the formula I, are also used as photoinitiators. The invention therefore also relates to the use of compounds of the formula I, and of the polymers which can be prepared therefrom and which have side groupings of the formula I′, as initiators for the photopolymerisation of ethylenically unsaturated compounds or for the photochemical crosslinking of polyolefines, and also mixtures of (A) a compound of the formula I or a polymer with side groupings of the formula I′ and (B) an organic amine, as initiators for the photopolymerisation of ethylenically unsaturated compounds or for the photochemical crosslinking of polyolefines.

The organic amines used can be aliphatic, aromatic, araliphatic, cycloaliphatic or heterocyclic amines. They can be primary, secondary or tertiary amines. Examples are: butylamine, dibutylamine, tributylamine, cyclohexylamine, benzyldimethylamine, di-cyclohexylamine, triethylamine, phenyl-diethanolamine, piperidine, piperazine, morpholine, pyridine, quinoline, ethyl p-dimethylaminobenzoate or Michler's ketone (4,4′-bis-dimethylaminobenzophenone).

Preferred mixtures are those consisting of (A) a compound of the formula I in which the group —CO—$(Y)_{\overline{n-1}}$Q is in the 1-position or 3-position and X, Z, Y, Q and n have the preferred meaning defined above and (B) an aliphatic tertiary amine, an alkyl p-dimethylaminobenzoate or Michler's ketone.

Examples of aliphatic tertiary amines are trimethylamine, triethylamine, tri-isopropylamine, tributylamine, dodecyl-dimethylamine, octyl-dimethylamine, triethanolamine, tris-(hydroxypropyl)-amine, N-methyl-diethanolamine or N-butyl-diethanolamine. Particularly preferred mixtures are those consisting of (A) a compound of the formula I, in which the group —CO—$(Y)_{\overline{n-1}}$Q is in the 1-position or 3-position and X, Z, Y, Q and n have the preferred meanings defined above and (B) triethanolamine or a $C_{1-4}$-alkyldiethanolamine.

The preferred mixtures mentioned preferably contain the compounds of the formula I and the organic amines in a weight ratio of 4:1 to 1:4.

Photopolymerisable compounds are, for example, unsaturated monomers, such as esters of acrylic acid or methacrylic acid, for example methyl acrylate, ethyl acrylate, n- or tert.-butyl acrylate, isooctyl acrylate or hydroxyethyl acrylate, methyl methacrylate or ethyl methacrylate, ethylene diacrylate, butanediol diacrylate, hexanediol diacrylate, neopentyl diacrylate, trimethylpropane trisacrylate, pentaerythritol tetraacrylate or pentaerythritol tris-acrylate; acrylonitrile, methacrylonitrile, acrylamide, methacrylamide and N-substituted (meth)-acrylamides; vinyl esters, for example vinyl acetate, vinyl propionate, vinyl acrylate or vinyl succinate; other vinyl compounds, such as vinyl ethers, vinyl ketones vinyl sulfones, styrene, alkylstyrenes, halogenostyrenes, divinylbenzene, N,N′-divinylurea, vinylnaphthalene, N-vinylpyrrolidone, vinyl chloride or vinylidene chloride; allyl compounds, such as diallyl phthalate, diallyl maleate, triallyl isocyanurate, triallyl phosphate or ethylene glycol diallyl ether and the mixtures of such unsaturated monomers.

The mixtures according to the invention are particularly suitable for the photopolymerisation of acrylic acid esters and mixtures thereof.

Further examples are unsaturated acrylic resins. These include, for example, reaction products of polyepoxides (epoxide resins) with acrylic acid or methacrylic acid or reaction products of polyisocyanates with hydroxyalkyl acrylates, and also the reaction products of hydroxyl group-containing polyesters or polyethers with acrylic acid or methacrylic acid. These unsaturated acrylic resins are in most cases used in a mixture with one or more acrylates of a mono-, di- or poly-alcohol, for example, ethyl acrylate, butyl acrylate, benzyl acrylate, 2-ethylhexyl acrylate or 2-hydroxypropyl acrylate, ethylene glycol diacrylate, propylene glycol diacrylate, butanediol diacrylate, hexamethylene diacrylate, trimethylolpropane tris-acrylate or pentaerythritol tetraacrylate.

The invention also relates to photopolymerisable systems consisting of (a) at least one ethylenically unsaturated compound, (b) a mixture, according to the definition, of (A) and (B) and, if desired, (c) other additives, such as inhibitors, stabilisers, UV-absorbers, fillers, pigments, dyes, thixotropic agents and levelling assistants, for example silicone oil.

The inhibitors, which are intended to provide protection against premature polymerisation, in particular during the preparation of the system by mixing the components, are, for example, hydroquinone, hydroquinone derivatives, p-methoxyphenol or β-naphthol. UV-absorbers which can be used are, for example, those of the benztriazole or benzophenone type. Suitable fillers are, for example, silica, talc or gypsum.

Preferred photopolymerisable systems of this type are those in which (a) and (c) are present in proportions of 99.5–80% by weight and (b) is present in a proportion of 0.5–20% by weight, the mixture (A) preferably consisting of a compound of the formula I in which the group —CO—$(Y)_{n-1}$Q is in the 1-position or 3-position and X, Z, Y, Q and n have the preferred meanings defined above.

An acrylic acid ester or a mixture of several acrylic acid esters is preferably used as component (a).

It is also possible to use combinations with known photoinitiators which form free radicals by photofragmentation, for example benzoin ethers, dialkoxyacetophenones or benzil ketals.

The initiator mixtures according to the invention are of great importance for the photocuring of printing inks and white-pigmented coatings, since the drying time of the binder is a decisive factor for the production rate of graphic products and should be of the order of magnitude of fractions of a second. The initiators according to the invention are also very suitable for photocurable systems for the production of printing plates.

A further field of application is the UV-curing of metal coatings, for example in the lacquer-coating of sheet metal for tubes, cans or bottle tops, and also the UV-curing of plastic coatings, for example floor coverings or wall coverings based on PVC.

Examples of the UV-curing of paper coatings are the colourless lacquer-coating of labels, gramophone record sleeves or book jackets.

The mixtures according to the invention can also be used as initiators for photochemical crosslinking of polyolefines. Polyolefines which can be used are, for example, polypropylene, polybutylene, polyisobutylene and copolymers, for example ethylene/propylene copolymers, but preferably polyethylene of low, moderate or high density.

The addition of the preferred photoinitiators to the photopolymerisable systems is generally effected by simple stirring-in, since most of these systems are liquid or readily soluble. Usually, a solution of the initiators is obtained and this ensures uniform distribution of the initiators and also transparency of the polymers.

The polymerisation is effected by the known methods for photopolymerisation by irradiation with light which is rich in short-wave radiation. Suitable light sources are, for example, medium pressure, high pressure and low pressure mercury radiant lamps and also superactinic fluorescent tubes which have their emission maxima in the range between 250 and 450 nm.

For the photochemical crosslinking of polyolefines, the photoinitiator is added to the polyolefins before or during processing for shaping, for example by mixing in powder form or by mixing with the plasticised polyolefine. Crosslinking is effected by irradiating the shaped article in solid form, for example in the form of films or fibres.

(I) PREPARATION EXAMPLES

EXAMPLE 1

Dry sodium thiophenolate prepared from 7.5 g (0.33 gram equivalent) of sodium, 300 ml of methanol and 36 ml (0.33 mol) of thiophenol is dissolved in 300 ml of dimethylsulfoxide, and 80.4 g (0.3 mol) of 3-nitrophthalic acid N-phenylimide are added. The reaction mixture is heated at 50° C. for 90 minutes and then poured into a mixture of 300 ml of water and 300 ml of anhydrous acetic acid. The resulting suspension is filtered with suction and the product is dried at 80° C./13,000 Pa. 100 g (100% of theory) of 3-phenylthiophthalic acid N-phenylimide are obtained.

99.4 g (0.3 mol) of 3-phenylthiophthalic acid N-phenylimide are suspended in 1,326 ml of a 20% sodium hydroxide solution and the suspension is heated at 100° C. for 30 minutes, with stirring. After cooling, the alkaline suspension is acidified with 672 ml of 37% hydrochloric acid, with stirring. After one hour the fine suspension is filtered with suction, the material on the suction filter is suspended, whilst till wet, in 882 ml of 37% hydrochloric acid and the suspension is refluxed for one hour. The reaction mixture is cooled, the resulting fine suspension is filtered with suction and the product is dried at 80° C./13,000 Pa. 69.4 g (85 of theory) of 3-phenylthiophthalic acid are obtained.

69 g (0.25 mol) of 3-phenylthiophthalic acid and 700 ml of polyphosphoric acid are heated at 200° C. for 90 minutes, with stirring, then cooled and stirred into 3,000 ml of water. After one hour the resulting suspension is filtered with suction and the material on the suction filter is washed with water and dried at 80° C. The resulting crude product is dissolved in 350 ml of hot N,N-dimethylformamide, animal charcoal is added and the mixture is filtered. The filtrate is diluted with five times the amount of water, the resulting suspension is filtered and the product is washed with water and dried. 63 g (98% of theory) of thioxanthone-1-carboxylic acid are obtained; melting point 259° C. The acid obtained in this way can be further used direct.

82 g (0.32 mol) of thioxanthone-1-carboxylic acid in 460 ml of thionyl chloride are refluxed for 5 hours. The resulting dark, clear solution is evaporated to dryness. 87.5 g (100% of theory) of thioxanthone-1-carboxylic acid chloride are obtained.

11 g (0.04 mol) of thioxanthone-1-carboxylic acid chloride and 10.4 g (0.08 mol) of 2-hydroxyethyl methacrylate in 170 ml of dioxan are heated at 80° C. for 3 hours and the mixture is then evaporated to dryness. The solid residue is stirred with 100 ml of water and the pH of the resulting suspension is adjusted to 8 with a 3% sodium bicarbonate solution. The crude product is then extracted with 200 ml of methylene chloride, the extract is dried over solid sodium sulfate and the methylene chloride is evaporated. The residue is dissolved in 100 ml of methanol and the solution is filtered with 4 g of animal charcoal. The product which has crystallised out is dissolved in 1,200 ml of diethyl ether and extracted with 50 ml of 1% sodium hydroxide solution. The ether phase is washed with water and dried over sodium sulfate. The ethereal solution is then stabilised with 0.05% by weight of 2,6-di-tert.-butyl cresol and concentrated. 7.7 g (52% of theory) of β-(methacryloyloxy)ethyl thioxanthone-1-carboxylate are obtained; melting point 112°–113° C.

IR spectrum (chloroform): 1740 cm$^{-1}$ (—COOR); 1660 cm$^{-1}$ (—CO—).

Analysis for $C_{20}H_{16}O_5S$ (molecular weight 368.34): Calculated: C, 65.22%; H, 4.37%; S, 8.68%. Found: C, 63.8%; H, 4.10%; S, 8.41%.

EXAMPLE 2

18.4 g (0.06 mol) of the sodium salt of thioxanthone-1-carboxylic acid (prepared by reacting thioxanthone-1-carboxylic acid with NaOH), 14.5 g (0.18 mol) of 2-chloroethanol and 0.18 g of diethylamine are refluxed at 130° C. for 4 hours. After cooling the reaction mixture, this is twice boiled up with, in each case, 100 ml of dioxan and filtered hot. The dioxan extracts are evaporated to dryness. The residue is recrystallised from 1,000 ml of methanol with the addition of animal charcoal. 13.2 g (73.3% of theory) of β-hydroxyethyl thioxanthone-1-carboxylate are obtained; melting point 169° C.

IR spectrum (chloroform): 1750 cm$^{-1}$(—COOR); 1660 cm$^{-1}$(—CO—).

Analysis for $C_{16}H_{12}O_4S$ (molecular weight 300.33): Calculated: C, 64.04%; H, 4.0%; S, 10.7%. Found: C, 63.8%; H, 4.0%; S, 10.6%.

EXAMPLE 3

90.2 g (0.726 mol) of p-thiocresol are dissolved in 600 ml of N,N-dimethylformamide, after which 31.7 g (0.792 mol) of finely powdered sodium hydroxide are added. After stirring for half an hour at 20°–25° C., 158.0 g (0.660 mol) of dimethyl nitroterephthalate are added to the homogeneous solution, and the reaction mixture is stirred for 1.5 hours at 70° C. After cooling to 20°–25° C., 1,000 ml of water are added and the precipitate which has separated out is filtered off. 275 g of moist product are obtained. This is heated in a solution of 89.5 g of KOH in 1,200 ml of methanol for one hour under reflux. The mixture is cooled to 20°–25° C., 1,000 ml of water and a little active charcoal are added and the resulting mixture is filtered after stirring for half an hour. The filtrate is freed from methanol in a rotary evaporator and the residual aqueous phase is extracted with three times 200 ml of methylene chloride. The precipitate formed after acidifying the aqueous phase with sulfuric acid is filtered off and washed with water. After drying in vacuo at 80° C., 140 g (74% of theory) of 2-(4-methylphenylthio)-terephthalic acid remain; melting point >250° C.; IR spectrum (KBr): 1690 cm$^{-1}$.

Elementary analysis for $C_{15}H_{12}O_4S$ (molecular weight 288.32): Calculated: C, 62.49%; H, 4.20%. Found: C, 62.56%; H, 4.28%.

The 2-(4-methylphenylthio)-terephthalic acid is treated with chlorosulfonic acid at between 5° and 10° C., after which the reaction mixture is poured onto ice and the thioxanthone-7-methyl-3-carboxylic acid which has precipitated is filtered off and dried in vacuo at 100° C.; yield 99% of theory; IR spectrum (KBr): 1640 cm$^{-1}$; UV spectrum (N,N-dimethylformamide): $\lambda_{max.}=395$ nm, $\epsilon=5733$.

80 g (0.30 mol) of the thioxanthone-7-methyl-3-carboxylic acid obtained are refluxed with 650 ml of thionyl chloride for 2 hours, after which excess thionyl chloride is distilled off. The residue is heated with 500 ml of ethylene glycol for 12 hours at 80° C., with good stirring. 200 ml of water are added to the reaction mixture at 20°–25° C. and the precipitate is filtered off. After drying at 70° C. in vacuo, 76.8 g (81% of theory) of yellow, crystalline β-hydroxyethyl thioxanthone-7-methyl-3-carboxylate with a melting point of 147°–164° C. remain. IR spectrum (KBr): 3450 cm$^{-1}$, 1730 cm$^{-1}$, 1645 cm$^{-1}$ and 1605 cm$^{-1}$.

EXAMPLE 4

Using the procedure described in Example 3, 5 g (0.019 mol) of thioxanthone-7-methyl-3-carboxylic acid are converted to the acid chloride using 50 ml of thionyl chloride, and the acid chloride is treated with 50 ml of diethylene glycol. After adding 100 ml of water and drying the resulting precipitate, 5.0 g (73% of theory) of the yellow diethylene glycol ester of thioxanthone-7-methyl-3-carboxylic acid are obtained; melting point 104°–109° C.

EXAMPLE 5

Using the procedure described in Example 3, 3.1 g (42% of theory) of the waxy, yellow triethylene glycol ester of thioxanthone-7-methyl-3-carboxylic acid, which has a melting range of 38°–75° C., are obtained from 5 g of thioxanthone-7-methyl-3-carboxylic acid, 50 ml of thionyl chloride and 60 ml of triethylene glycol.

EXAMPLE 6

Using the procedure described in Example 3, 6.32 g (100% of theory) of yellow β-carboxyethyl thioxanthone-7-methyl-3-carboxylate with a melting point >250° C. are obtained from 5 g of thioxanthone-7-methyl-3-carboxylic acid, 60 ml of thionyl chloride and 40 ml of 3-hydroxypropionic acid.

EXAMPLE 7

8.34 g (0.03 mol) of the sodium salt of thioxanthone-1-carboxylic acid and 0.1 ml of triethylamine are heated in 15 ml of epichlorohydrin at 130° C. until a dark, homogeneous solution has formed, and the solution is then kept at this temperature for 3 hours. The reaction mixture is then diluted with 50 ml of dioxan, heated to reflux and cooled, and the sodium chloride which has precipitated out is filtered off with suction. The solvent is evaporated and the residue is stirred with 15 ml of diethyl ether. The crude product which has crystallised out is filtered off with suction. Both the product which has crystallised out and the mother liquor are purified through a silica gel column (solvent system chloroform/acetone in a volume ratio of 19:1). The products obtained after chromatography are recrystallised from methanol. 7.54 g (80.5% of theory) of glycidyl 1-thioxanthone-1-carboxylate are obtained; melting point 115°–117° C.

IR spectrum (chloroform): 1750 cm$^{-1}$ (—COOR); 1660 cm$^{-1}$ (—CO—).

UV spectrum: $\lambda_{max.}$ = 385 nm, $\epsilon$ = 6600.

Elementary analysis for $C_{17}H_{12}O_4S$ (molecular weight 312.34) Calculated: C, 65.38%; H, 3.88%; S, 10.27%. Found: C, 64.62%; H, 3.87%; S, 10.19%.

EXAMPLE 8

0.6 g (0.01 mol) of ethanolamine are mixed with 5.6 ml of ethanolic hydrochloric acid (19.5%). The ethanol is then distilled off, to dryness. 5.5 g (0.02 mol) of thioxanthone-1-carboxylic acid chloride are dissolved in 550 ml of acetonitrile and the solution is mixed with the ethanolamine hydrochloride previously prepared. The reaction mixture is refluxed for 60 hours and then evaporated to dryness. The residue is stirred with 200 ml of water and insoluble constituents are filtered off with suction. The solution is rendered alkaline with 10% aqueous potassium carbonate and immediately extracted by shaking with twice 200 ml of diethyl ether, after which the diethyl ether is evaporated. 0.67 g (20% of theory) of the hydrochloride of β-aminoethyl thioxanthone-1-carboxylate is obtained; melting point 231° C. (with decomposition).

IR spectrum (KBr): 1755 cm$^{-1}$ (—COOR); 1660 cm$^{-1}$ (—CO—).

UV spectrum (H$_2$O) $\lambda_{max.}$ = 390 nm, $\epsilon$ = 5000.

Elementary analysis for $C_{16}H_{14}ClNO_3S$ (molecular weight 335.8): Calculated: C, 57.23%; H, 4.20%; Cl, 10.56%; N, 4.17%; S, 9.55%. Found: C, 57.75%; H, 4.5%; Cl, 10.2%; N, 4.2%; S, 9.2%.

EXAMPLE 9

19 g (0.0683 mol) of the sodium salt of thioxanthone-1-carboxylic acid, 190 ml of β-chloroethyl vinyl ether and 0.8 g (0.0033 mol) of triethylammonium iodide are refluxed for 6 hours in a 250 ml three-necked flask. The reaction solution is cooled and filtered and the filtrate is then evaporated. The reaction product is recrystallised from ligroin. This yields 21.2 g (95.1% of theory) of the β-ethylvinyl ether of thioxanthone-1-carboxylic acid, which has a melting point of 163°–164° C. and an elementary analysis of: Calculated: C, 66.24%; H, 4.33%; S, 9.82%. Found: C, 65.92%; H, 4.21%; S, 9.74%.

UV absorption spectrum: $\lambda_{max.}$ 258, 289, 302 and 384 nm; $\epsilon_{max.}$ = 43400, 4700, 3900 and 7000.

EXAMPLE 10

20 g (0.078 mol) of thioxanthone-1-carboxylic acid and 0.1 g of Li$_2$(PdCl$_4$) in 400 ml of vinyl acetate are refluxed for 21 hours in a 750 ml sulfonation flask. The greyish suspension is cooled to 50° C. and 5 g of active charcoal are added. After 15 minutes, the suspension is filtered with suction and the material on the suction filter is boiled in 1 liter of methylene chloride for 15 minutes and the mixture is filtered hot. The solution is evaporated and the resulting yellow powder is recrystallised from 500 ml of toluene, with active charcoal. This yields 15 g (68.12% of theory) of vinyl thioxanthone-1-carboxylate with a melting point of 220°–222° C. and an elementary analysis of: Calculated: C, 68.07%; H, 3.57%; O, 17.0%; S, 11.36%. Found: C, 67.75%; H, 3.56%; O, 17.23%; S, 11.21%.

$^1$H-NMR spectrum (100 MHz, CDCl$_3$+DMSO-d$_6$): 1H: 8.5 ppm, 7H: 7.4–8.8 ppm, 2H: 4.65–5.0 ppm.

UV spectrum: 386 nm, $\lambda$ = 6800.

EXAMPLE 11

1.22 g (0.02 mol) of ethanolamine are added dropwise in the course of 10 minutes to 2.75 g (0.01 mol) of thioxanthone-1-carboxylic acid chloride in 40 ml of dioxan, with stirring. The resulting pale reaction mixture is stirred for a further 24 hours and then concentrated to dryness. 200 ml of water are added to the solid residue, the mixture is extracted with 2 × 100 ml of chloroform and the extracts are concentrated to dryness. 2.02 g (67.5% of theory) of thioxanthanone-1-carboxylic acid β-hydroxyethylamide are obtained; melting point 202° C. IR spectrum (KBr): 1670 cm$^{-1}$ (—CO—NH—), 1640 cm$^{-1}$ (—CO—).

Elementary analysis for $C_{16}H_{13}NO_3S$ (molecular weight 299): Calculated: C, 64.2%; H, 4.4%; N, 4.7%; S, 10.7%. Found: C, 64.3%; H, 4.4%; N, 4.6%; S, 10.5%.

(II) USE EXAMPLES

EXAMPLE 1

2 g (0.007 mol) of vinyl thioxanthone-1-carboxylate are dissolved in 49 ml of N,N-dimethylformamide, under nitrogen, in a 100 ml three-necked flask. 0.02 g (0.00012 mol) of azoisobutyronitrile, dissolved in 1 ml of N,N-dimethylformamide, is added at 70° C., and the mixture is polymerised under a nitrogen atmosphere for 24 hours. The solution is precipitated in 250 ml of methanol and the resulting polymer is dried in vacuo at 40° C. (polymer No. 1).

465.5 g (1.963 mol) of the β-(methacryloyloxy)ethyl ester of dimethylmaleimide (prepared in accordance with German Offenlegungsschrift No. 2,626,769) are dissolved together with 49.15 g (0.49 mol) of ethyl acrylate in 960 ml of 1-acetoxy-2-ethoxyethane, under nitrogen. A solution of 3.86 g of azoisobutyronitrile in 25 ml of 1-acetoxy-2-ethoxyethane is allowed to run in at 80° C., under a nitrogen atmosphere, and the mixture is then polymerised for 6 hours. The solution is stabilised, whilst still hot, with 2.57 g of 2,6-di-tert.-butyl-p-cresol. Viscosity of the solution, measured with a Höppler falling ball viscometer in accordance with DIN 53,015 = 829. 10$^3$ Pa s (polymer No. 2); mean molecular weight (measured by light scattering in chloroform) = 1,000,000. 2.7% by weight of (polymer No. 1) are added, as the sensitiser, to this polymer solution. Using the polymer solution, which has been diluted to a solids content of 15% by weight, copper sheets are so coated, by whirler-coating (500 revolutions/minute for 1 minute), that, after drying, a 1–3μ thick coating of polymer is formed on the copper. The coated sheets are exposed through a negative original (step wedge, Stauffer 21-step sensitivity guide) using a high-pressure mercury discharge lamp 400 at a distance of 60 cm from the vacuum table. After exposure, the image is developed for 2 minutes in a 1,1,1-trichloroethane bath by which means the portions which have not been cross-linked are dissolved out. The resulting relief image of the recorded step wedge is rendered visible by etching the exposed parts of the copper with a 50% FeCl$_3$ solution. Last step recorded (slightly etched) after an exposure time of:

1 minute step 1
3 minutes step 4

6 minutes step 6
12 minutes step 7.

EXAMPLE II 0.64 g of a commercially available copolymer of ethylene and maleic anhydride (1:1) with a mean molecular weight of 20,000, 1 g (0.0035 mol) of β-hydroxyethyl thioxanthone-1-carboxylate and 15 ml of tetrahydrofuran are stirred for 72 hours at 66° C. in a 100 ml three-necked flask. 1.2 g of polymer (polymer No. 3) are obtained.

EXAMPLE III 2.5 g (0.008 mol) of thioxanthone-1-carboxylic acid β-ethylvinyl ether, dissolved in 70 ml of toluene, are initially introduced into a 100 ml three-necked flask. 44 ml of toluene are distilled off under nitrogen, through a descending condenser. The resulting yellow solution is cooled to −15° C. At this temperature 0.05 g of freshly distilled boron trifluoroethyl etherate are added. The solution is stirred at −15° to −10° C. for 3 hours. 75 ml of methanol are added to the yellow suspension, the suspension is then filtered with suction and the product is dried in vacuo at 40° C. This yields 2.2 g (88% of theory) of polythioxanthone-1-carboxylic acid β-ethylvinyl ether (polymer No. 4). 2.7% by weight of this polymer are added, as the sensitiser, to the polymer solution described in Example I, paragraph 2. Using the polymer solution, which has been diluted to a solids content of 15% by weight, copper sheets are then coated, and subsequently exposed, in the manner described in Example I.

Last step recorded after an exposure time of:
3 minutes step 1
6 minutes step 3
12 minutes step 5.

EXAMPLE IV 0.744 g of a copolymer of ethylene and maleic anhydride (1:1, with a mean molecular weight of 20,000), 0.8 g (0.0024 mol) of the hydrochloride of β-aminoethyl thioxanthone-1-carboxylic acid and 1.5 ml of pyridine are stirred for 24 hours at 24° C. in a 10 ml three-necked flask. The reaction mixture is then diluted with 5 ml of pyridine and precipitated in 300 ml of 1 N HCl. The resulting suspension is filtered with suction and the reaction product is dried in vacuo at 40° C. This yields 1.3 g of polymer with an intrinsic viscosity of 0.18 dl/g in chloroform (polymer No. 5).

EXAMPLE V 7.2 g of a polyacrylic acid with a mean molecular weight of 30,000 and 21.86 g (0.07 mol) of glycidyl thioxanthone-1-carboxylate are dissolved in 260 ml of cyclohexanone with the addition of 0.3 g of tetramethylammonium bromide and the solution is stirred for 6 hours at 120° C. under nitrogen. The viscous, slightly yellow solution is precipitated in 3 liters of diethyl ether. This yields 23.8 g (82% of theory) of a polymer which has an elementary analysis of: Calculated: C, 61.56%; H, 4.3%; O, 26.42%; S, 7.72%. Found: C, 61.43%; H, 4.27%; O, 26.43%; S, 7.87%. Intrinsic viscosity of the polymer in chloroform: 0.28 dl/g.

EXAMPLE VI 20 g (0.054 mol) of β-(methacryloyloxy)-ethyl thioxanthone-1-carboxylate and 0.2 g (0.0012 mol) of azoisobutyronitrile are dissolved in 80 ml of tetrahydrofuran, under nitrogen, and the solution is refluxed for 8 hours. The slightly viscous solution is precipitated in 1 liter of diethyl ether and the resulting white polymer is dried for 12 hours at 40° C. in vacuo. 16.35 g (82% of theory) of a white polymer are obtained; intrinsic viscosity in chloroform: 0.18 dl/g.

EXAMPLE VII 38.056 g (0.103 mol) of β-(methacryloyloxy)-ethyl thioxanthone-1-carboxylate, 7.445 g (0.103 mol) of acrylic acid and 0.455 g (0.003 mol) of azoisobutyronitrile are dissolved in 205 ml of tetrahydrofuran, under nitrogen, and the solution is refluxed for 8 hours. The colourless solution is precipitated in 2.5 liters of diethyl ether and the resulting powder is dried in vacuo at 20°–25° C. 34.4 g (75.6% of theory) of a white polymer are obtained; intrinsic viscosity in chloroform: 0.25 dl/g.

EXAMPLE VIII 12.88 g of the diethylene glycol ester of thioxanthone-7-methyl-3-carboxylic acid and 5 g of a copolymer of methyl vinyl ether and maleic anhydride (1:1) are dissolved in 180 ml of tetrahydrofuran with the addition of 1 ml of pyridine and the solution is stirred for 48 hours at 70° C. The yellow polymer solution is precipitated in 2 liters of diethyl ether and the resulting polymer powder is dried in vacuo at 40° C. 16.5 g (92.3% of theory) of polymer are obtaied; intrinsic viscosity in chloroform: 0.30 dl/g.

EXAMPLE IX

A white lacquer is prepared in accordance with the following recipe:
1.89 g of Plex 6631 (acrylic resin from Röhm & Haas, Federal Republic of Germany),
0.52 g of 2-hydroxypropyl acrylate
2.40 g of titanium dioxide RTC-2 (titanium dioxide from BTP Thioxide, England)
0.13 g of N-methyldiethanolamine
1.29 g of hexanediol diacrylate and
0.03 g of β-hydroxyethyl thioxanthone-1-carboxylate.

The mixture is ground with the aid of a disc grinding machine with the disc under a weight of 7.5 kg (200 revolutions). The white lacquer prepared in this way is applied to glass plates using a 40 μm doctor. The samples are irradiated using a UV exposure apparatus (standard Hg vapour lamp; lamp power 80 watts/cm, distance of the lamp from the plate 11 cm, conveyor belt speed=50 m/minute). The following four tests are used to assess the curing of the white lacquer samples:

1. Wiping resistance: 4.
The number of passes of the sample through the irradiation apparatus before a wipe-resistant surface is obtained is determined.

2. Pendulum hardness: 142.
The samples are passed 10 times through the UV irradiation apparatus. The pendulum hardness is then determined in accordance with DIN 53,157.

3. Gloss: 81.
The samples are passed 10 times through the UV irradiation apparatus. The gloss is measured with the aid of a multi-gloss apparatus at an angle of 60° (DIN 67,530).

4. Whiteness: 0.

The samples are passed 10 times through the UV irradiation apparatus. The whiteness (yellowness index) is determined with the aid of a colour-measuring apparatus.

What is claimed is:

1. A compound of the formula I

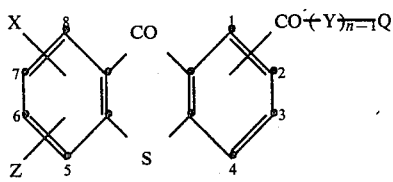

in which n is the number 1 or 2, X is hydrogen, halogen, —CN, —OH, —SH, —$NO_2$, —$NH_2$, phenylsulfonyl or alkylsulfonyl, alkyl, alkoxy, alkylthio, N,N-dialkylamino or —CO-alkyl having, in each case, 1–4 C atoms in the alkyl moieties, Z is hydrogen, halogen, —OH, —SH or alkyl, alkoxy, alkylthio or N,N-dialkylamino having, in each case, 1–4 C atoms in the alkyl moieties, Y is —$OR_1$—, —$SR_1$— or —$N(R_2)R_1$—, $R_1$ is straight-chain or branched alkylene having a total of 2–23 C atoms and 2–13 C atoms in the main chain, cyclopentylene, cyclohexylene, phenylene,

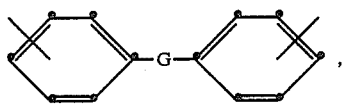

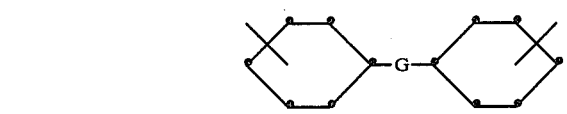

or, if n is 2 and Q is —OH or —OCO—C(R″)=$CH_2$, also —($CH_2CH_2O$)$_x$—$CH_2CH_2$—, $R_2$ is hydrogen or straight-chain or branched alkyl having a total of 1–23 C atoms and 1–13 C atoms in the main chain, G is —$CH_2$—, —$CH_2CH_2$—, —$C(CH_3)_2$—, —O—, —$SO_2$— or —NH—, x is an integer from 1 to 5, Q is

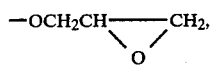

—$OCH_2$—COOH, —OCH=$CH_2$, —$OCH_2$CH=$CH_2$, —$SCH_2$CH=$CH_2$ or —$NHCH_2$CH=$CH_2$ if n is 1, and is —OH, —SH, —$NH_2$, —NHR′, —$SO_3$H, —COOH, —COCl, —NCO, —OCO—C(R″)=$CH_2$, —S-CO—C(R″)=$CH_2$, —NHCO—C(R″)=$CH_2$, —OCH=$CH_2$,

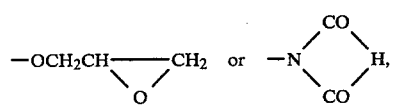

if n is 2, or is also —CH=$CH_2$ if $R_1$ is alkylene or phenylene, and R′ is alkyl having 1–5 C atoms and R″ is hydrogen or methyl, or a salt of a compound of the formula I in which Q is —$NH_2$ or —NHR′.

2. A compound of the formula I according to claim 1, in which Z is hydrogen, n, X, Y and Q are as defined and the grouping —CO(Y)$_{n-1}$Q is in the 1-position or 3-position.

3. A compound of the formula I according to claim 1, in which X is hydrogen and Z is hydrogen or methyl or methoxy bonded in the 7-position, the group —CO—(Y)$_{n-1}$Q is in the 1- or 3-position, n is 1 and Q is

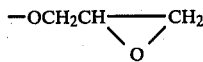

or —OCH=$CH_2$, or n is 2, Y is —$OR_1$— or —$NHR_1$—, $R_1$ is alkylene having 2–6 C atoms or, if Q is —OH or —OCO—C(R″)=$CH_2$, also —$CH_2CH_2OCH_2CH_2$— or —($CH_2CH_2O$)$_2CH_2CH_2$—, and Q is —OH, —$NH_2$, —$NHCH_3$, —COOH, —COCl, —OCO—C(R″)=$CH_2$, —OCH=$CH_2$,

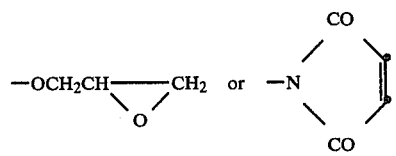

or a salt of such a compound of the formula I, in which Q is $NH_2$ or —$NHCH_3$, with an inorganic acid.

4. A compound of the formula I according to claim 3, in which Q is —OCH=$CH_2$ if n is 1, and is —OH, —$NH_2$, —OCH=$CH_2$ or —OCO—C(R″)=$CH_2$ if n is 2, or a salt of such a compoun of the formula I, in which Q is —$NH_2$, with HCl.

5. A compound according to claim 1, of the formula

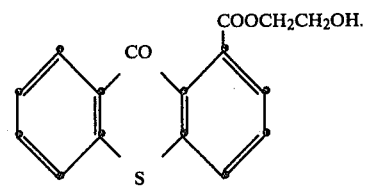

6. A compound according to claim 1, of the formula

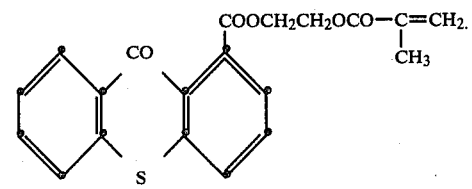

* * * * *